United States Patent [19]

Schrott et al.

[11] Patent Number: 4,990,649
[45] Date of Patent: Feb. 5, 1991

[54] AZULENESQUARIC ACID DYES THAT CONTAIN URETHANE GROUPS

[75] Inventors: Wolfgang Schrott, Ludwigshafen; Peter Neumann, Mannheim; Michael Schmitt, Ludwigshafen; Sibylle Brosius, Mannheim; Klaus D. Schomann, Ludwigshafen; Harald Kuppelhamier, Heidelberg, all of Fed. Rep. of Germany

[73] Assignee: BASF Aktiengesellschaft, Ludwigshafen, Fed. Rep. of Germany

[21] Appl. No.: 347,439

[22] Filed: May 2, 1989

[30] Foreign Application Priority Data

May 11, 1988 [DE] Fed. Rep. of Germany ....... 3816068

[51] Int. Cl.$^5$ ............... C07C 271/12; C07C 271/28; C07C 271/24; C09B 69/00
[52] U.S. Cl. .................................. 560/25; 560/26; 560/115; 560/162; 560/166; 560/168; 260/404; 260/404.5
[58] Field of Search ............... 560/162, 166, 116, 168, 560/25, 26; 260/404, 404.5

[56] References Cited

U.S. PATENT DOCUMENTS

| | | | |
|---|---|---|---|
| 3,894,031 | 7/1975 | Hauck et al. | 560/162 X |
| 3,984,419 | 10/1976 | Hauck et al. | 560/162 X |
| 3,992,437 | 11/1976 | Shaw et al. | 560/162 X |
| 4,675,423 | 6/1987 | Schrott et al. | 556/136 |
| 4,806,664 | 2/1989 | Schrott et al. | 556/136 |

FOREIGN PATENT DOCUMENTS 3733173 12/1987 Fed. Rep. of Germany .

OTHER PUBLICATIONS

Angew. Chem. 78, p. 937, (1966), (Ziegenbein et al.).
Dyes and Pigments, vol. 8, pp. 381 to 388, (1987), (Kim et al.).

*Primary Examiner*—Floyd D. Higel
*Attorney, Agent, or Firm*—Oblon, Spivak, McClelland, Maier & Neustadt

[57] ABSTRACT

Azulenesquaric acid dyes of the formula

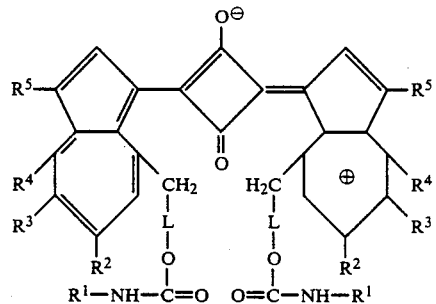

where
L is substituted or unsubstituted $C_1$–$C_{12}$-alkylene,
$R^1$ is $C_1$–$C_{20}$-alkyl, $C_5$–$C_7$-cycloalkyl or substituted or unsubstituted phenyl and
$R^2$, $R^3$, $R^4$ and $R^5$ are each independently of the others hydrogen or substituted or unsubstituted $C_1$–$C_{12}$-alkyl, with the proviso that when $R^5$ is hydrogen the positions of the substituents $CH_2$—L—O—CO—$NHR^1$ and $R^4$ on an azulene ring may also be interchanged within a ring in either or both of the azulene rings, derived from azulene intermediates that contain urethane groups, are suitable for use in an optical recording medium.

4 Claims, No Drawings

AZULENESQUARIC ACID DYES THAT CONTAIN URETHANE GROUPS

The present invention relates to azulenesquaric acid dyes that contain urethane groups and have the formula I

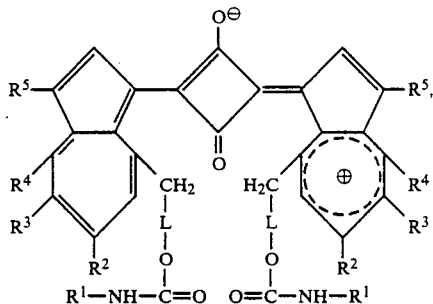

where
L is $C_1$–$C_{12}$-alkylene, which may substituted by phenyl,
$R^1$ is $C_1$–$C_{20}$-alkyl, $C_5$–$C_7$-cycloalkyl or substituted or unsubstituted phenyl and
$R^2$, $R^3$, $R^4$ and $R^5$ are identical or different and are each independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or cyano,
with the proviso that when $R^5$ is hydrogen the positions of the substituents $CH_2$—L—O—CO—$NHR^1$ and $R^4$ on an azulene ring may also be interchanged within a ring in either or both of the azulene rings, to intermediates therefor, and to an optical recording medium that contains the novel dyes.

Efficient manufacture of optical data recording media requires dyes having special properties. These dyes should show strong absorption between 700 and 900 nm in order to give layers that are writable with semiconductor lasers, be highly reflective in the layer in the near infrared (700–900 nm) in order to make possible a simple layered structure (without reflector layer), be highly soluble in order for example to be able to apply the thin storage layer to a base by spincoating, and be highly stable in thin layers.

Prior art storage materials fall short of one or more of these requirements.

It is an object of the present invention to provide novel dyes where the abovementioned defects do not appear at all or only to an extremely small extent.

We have found that this object is achieved by the azulenesquaric acid dyes of the formula I defined above.

Any of the alkylene and alkyl groups appearing in the abovementioned formula I may be either linear or branched.

In any substituted phenyl groups in the formula I, possible substituents are for example $C_1$–$C_4$-alkyl, $C_1$–$C_4$-alkoxy and halogen.

Preferred halogen is in each case fluorine, chlorine or bromine.

Radicals L are for example methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene, undecamethylene, dodecamethylene, phenylethylene, 1-phenyl-1,2-propylene and 2-phenyl-1,3-propylene.

Radicals $R^1$, $R^2$, $R^3$, $R^4$ and $R^5$ in the formula I are each for example methyl, ethyl, propyl, isopropyl, butyl, isobutyl, sec-butyl, tert-butyl, pentyl, isopentyl, neopentyl, tert-pentyl, 2-methylbutyl, hexyl, 2-methylpentyl, heptyl, octyl, 2-ethylhexyl, nonyl, decyl, undecyl or dodecyl.

Radicals $R^1$ are each further for example tridecyl, tetradecyl, pentadecyl, hexadecyl, heptadecyl, octadecyl, nonadecyl, eicosyl, cyclopentyl, cyclohexyl, cycloheptyl, phenyl, 2- or 4-methylphenyl, 2- or 4-methoxyphenyl, 2- or 4-chlorophenyl or 2,4-dichlorophenyl.

Radicals $R^2$, $R^3$, $R^4$ and $R^5$ are each further for example fluoromethyl, chloromethyl, difluoromethyl, trifluoromethyl, trichloromethyl, 2-fluoroethyl, 2-chloroethyl, 2-bromoethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 4-ethoxybutyl, 4-isopropoxybutyl, 5-ethoxypentyl, 6-methoxyhexyl, benzyl, 1-phenylethyl, 2-phenylethyl, 4-chlorobenzyl, 4-methoxybenzyl, 2-(4-methylphenyl)ethyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

Preference is given to azulenesquaric acid dyes of the formula I where $R^2$, $R^3$, $R^4$ and $R^5$ are each $C_1$–$C_6$-alkyl.

Preference is further given to azulenesquaric acid acid dyes of the formula I where $R^1$ is $C_1$–$C_{18}$-alkyl or cyclohexyl.

Particular preference is given to azulenesquaric acid dyes of the formula I where $R^2$ and $R^4$ are each methyl, $R^3$ and $R^4$ are each hydrogen, and L and R are each as defined above. These dyes conform to the formula Ia

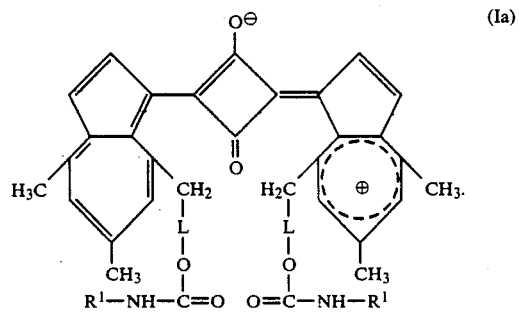

Further particular preference is given to azulenesquaric acid dyes of the formula I where $R^2$ and $R^4$ are each hydrogen, $R^3$ is isopropyl, $R^5$ is methyl and L and $R^1$ are each as defined above. These dyes conform to the formula Ib

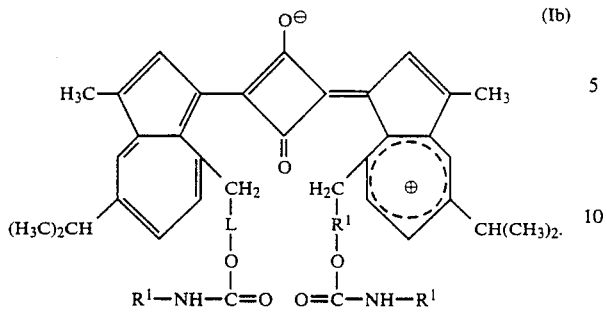

(Ib)

The dyes of the formula I are obtained from azulene derivatives of the formula II where L, $R^1$, $R^2$, $R^3$, $R^4$ and $R^5$ are each as defined above by reaction with squaric acid of the formula III in accordance with the following equation:

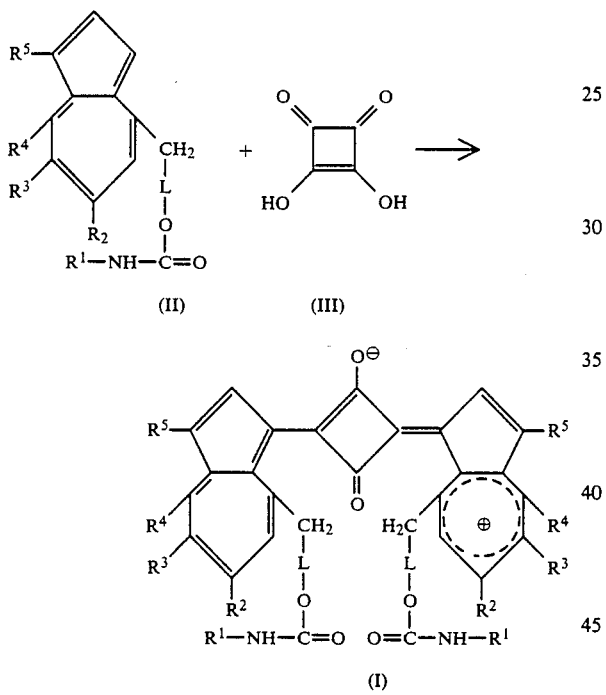

With those azulene derivatives of the formula II where $R^5$ is hydrogen, there are various positions on the five-membered ring for attachment of the squaric acid, which can give rise to isomeric products where the ring positions of substituents $CH_2$—L—O—CO—NH—$R^1$ and $R^4$ are, as stated above, interchanged. This is because a distinction must then be made between compounds where the bond to squaric acid is formed on that side where the substituent $CH_2$—L—O—CO—NH—$R^1$ is attached and those compounds where the bond to squaric acid is situated on that side where the substituent $R^4$ is attached. These isomeric compounds can be separated by chromatography. However, for applications in storage layers it is customary to use the mixed isomers.

The method of preparation is known per se and described for example in Angew. Chem. 78 (1966), 937, and in earlier German Patent Application DE-A-No. 3,733,173.

The present invention further provides novel azulenes that contain urethane groups and have the formula II

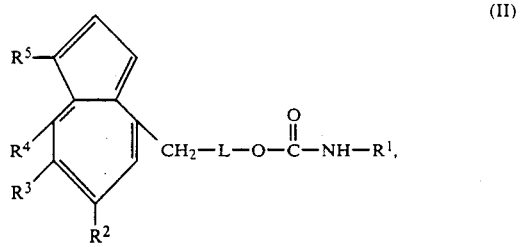

(II)

where

L is $C_1$–$C_{12}$-alkylene, which may be substituted by phenyl, $R^1$ is $C_1$–$C_{20}$-alkyl, $C_5$–$C_7$-cycloalkyl or substituted or unsubstituted phenyl and $R^2$, $R^3$, $R^4$ and $R^5$ are identical or different and are each independently of the others hydrogen or $C_1$–$C_{12}$-alkyl which may be substituted by halogen, $C_1$–$C_{12}$-alkoxy, phenyl, substituted phenyl, $C_1$–$C_{12}$-alkoxycarbonyl or cyano.

For examples of the radicals L, $R^1$, $R^2$, $R^3$, $R^4$ and $R^5$, see the foregoing recitation.

The azulene derivatives of the formula II which contain urethane groups are obtained for example by starting from the corresponding hydroxyalkylazulene derivatives. The preparation of these products is described for example in earlier German Patent Application DE-A-No. 3,733,173.

For instance, particular suitability for the reaction is possessed for example by those azulene derivatives of the formula IVa or IVb

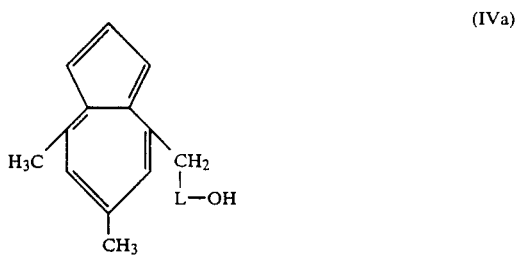

(IVa)

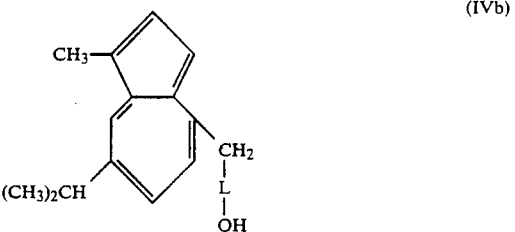

(IVb)

where L is in each case as defined above.

The reactants used with the hydroxyalkylazulene derivatives are organic monoisocyanates of the formula V $$R^1-N=C=O \qquad (V)$$

where $R^1$ is as defined above.

The hydroxyalkylazulene derivative is reacted with the organic monoisocyanate in a conventional manner, for example by reaction in an inert organic solvent (for example methylene chloride, 1,1,2-trichloroethane, toluene, naphtha or cyclohexane) at from 20° to 60° C. in the presence or absence of a catalyst (for example tertiary amines, tetraalkylammonium hydroxides or organic tin compounds). In general, the isocyanate is used in excess.

It is a further object of the present invention to provide a novel optical recording medium that contains azulenesquaric acid derivatives as storage materials and that is simple to manufacture, that is readily writable and subsequently also readily readable, ideally with a very high signal-to-noise ratio, and that is highly stable in the storage layers.

We have found that this object is achieved with an optical recording medium comprising a base and a thin radiation sensitive coating film containing a dye with or without a binder, where the dye has the formula I

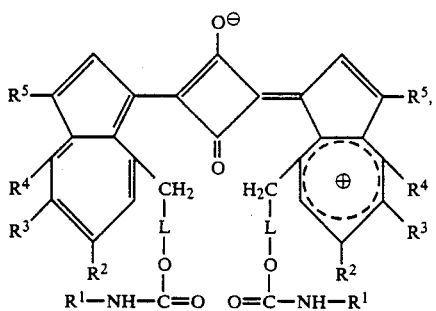

where
L is $C_1$-$C_{12}$-alkylene, which may be substituted by phenyl,
$R^1$ is $C_1$-$C_{20}$-alkyl, $C_5$-$C_7$-cycloalkyl or substituted or unsubstituted phenyl and
$R^2$, $R^3$, $R^4$ and $R^5$ are identical or different and are each independently of the others hydrogen or $C_1$-$C_{12}$-alkyl which may be substituted by halogen, $C_1$-$C_{12}$-alkoxy, phenyl, substituted phenyl, $C_1$-$C_{12}$-alkoxycarbonyl or cyano,
with the proviso that when $R^5$ is hydrogen the positions of the substituents $CH_2$—L—O—CO—$NHR^1$ and $R^4$ on an azulene ring may also be interchanged within a ring in either or both of the azulene rings.

Preference is given to an optical recording medium which contains azulenesquaric acid dyes of the formula I where $R^2$, $R^3$, $R^4$ and $R^5$ are each $C_1$-$C_6$-alkyl.

Preference is further given to an optical recording medium which contains azulenesquaric acid dyes of the formula I where $R^1$ is $C_1$-$C_{18}$-alkyl or cyclohexyl.

Particular preference is given to an optical recording medium which contains azulenesquaric acid dyes of the formula I where $R^2$ and $R^4$ are each methyl and $R^3$ and $R^5$ are each hydrogen.

Further particular preference is given to an optical recording medium which contains azulenesquaric dyes of the formula I where $R^2$ and $R^4$ are each hydrogen, $R^3$ is isopropyl and $R^5$ is methyl.

Advantageous bases are transparent bases, such as glass or plastics. Suitable plastics are for example poly(meth)acrylates, polycarbonates, polyesters, epoxies, polyolefins (for example polymethylpentene), polyamide, polyvinyl chloride, polystyrene and polyvinyl esters.

A preferred recording medium has a base made of polycarbonate or poly(meth)acrylates, but in particular polycarbonate.

Preference is further given to an optical recording medium which contains from 1 to 30% by weight, based on the dye, of binder.

The novel azulenesquaric acid dyes of the formula I have good optical characteristics. Moreover, pure dye layers based on the novel compounds are very stable. This is because to date no recrystallization of the pure dye layer has been observed and the addition of polymeric binders is thus not necessary. Furthermore, the light fastness (stability) is distinctly better than that of known methine dyes, so that the addition of stabilizers to the layer recipe can be restricted to a minimum. Another particular advantage is the good solubility of the novel dyes I in most organic solvents, so that these dyes can be spincoated directly (without protective layer) onto structured plastics substrates, in particular polycarbonate substrates.

As mentioned above, the spincoating solution preferably contains a binder in order to ensure the long term stability of the recording medium and in particular to adjust the spincoating solution to the most suitable viscosity. Preferably, the solution contains from 1 to 30% by weight, based on the level of dissolved solids in the spincoating solution, of a binder. Suitable binders are for example polyorganosiloxanes, epoxies, poly(meth)acrylates, polystyrene homopolymers and copolymers, polyvinylcarbazole, polyvinylpyrrolidone, polyimidazolecopolymers, polyvinyl ester copolymers, polyvinyl ether copolymers, polyvinylidene chloride copolymers, acrylonitrile copolymers, polyvinyl chloride or copolymers thereof, cellulose acetate and nitrocellulose.

A preferred recording medium has a binder based on a vinylpyrrolidone/vinyl acetate copolymer or on a polyvinyl chloride/polyvinyl ether copolymer.

The optical recording medium according to the invention is advantageously prepared by spincoating with a solution containing organic solvent, azulenesquaric acid dye I and an optional binder. Advantageously, this spincoating solution has a dissolved solids content of from 1 to 30% by weight, based on the solution.

Suitable solvents are for example propanol, isopropanol, butanol, diacetone alcohol, methyl ethyl ketone, toluene, bromoform, 1,1,2-trichloroethane and the mixtures thereof.

If desired, the solution may additionally contain up to 10% by weight, based on the level of dissolved solids in the spincoating solution, of additives, for example antioxidants, singlet oxygen quenchers or UV absorbers.

Preferably, the spincoating solution contains up to 5% by weight, based on the level of dissolved solids in the spincoating solution, of a mixture of a plurality of antioxidants, singlet oxygen quenchers and UV absorbers. If those types of antioxidants that likewise absorb the near infrared are to be included, for example nickel dithiolene complexes as described for example in DE-A No. 3,505,750, DE-A No. 3,505,751 or S. H. Kim, M. Matsuoka, M. Yomoto, Y. Tsuchiya and T. Kitao, Dyes and Pigments, 8 (1987), 381–388, the solution preferably contains up to 10% by weight thereof, based on the level of dissolved solids in the solution.

Spincoating is to be understood as meaning the application of solution to the rotating base, which conveniently has a round shape. However, it is also possible to apply the solution to the initially stationary base and then to set the base in rotation. The solution is conveniently applied to the base by means of a syringe or capillaries or by means of a mechanical pump.

The base generally rotates at a speed of 50–7000 rpm, preferably 500–5000 rpm, advantageously the speed being relatively low (about 500–2000 rpm) for the application of the solution and relatively high (about 5000–7000 rpm) for the subsequent spinning to dryness. The thickness of the laser light sensitive layer is from 40 to 160 nm, preferably from 80 to 120 nm. It depends on the speed of rotation, the concentration and viscosity of the spincoating solution, and the temperature.

In the optical recording medium according to the invention, the laser light sensitive layer is present in the form of a homogeneous, thin, smooth film of high optical quality. For instance, the reflectivity values are in general greater than 12%.

The novel recording medium, furthermore, is sufficiently sensitive at the wavelength of the laser light used; that is, irradiation with light pulses of a few nJ energy content and focused to a diameter $\leq 1$ μm gives pits with excellent signal-to-noise characteristics.

A suitable laser light source on account of the smallness of the component, its low energy requirements and the possibility of direct modulation of the optical output power through modulation of the electrical drive current is a solid state injection laser that emits in the near infrared, in particular an AlGaAs laser which operates within the wavelength range from about 700 to 900 nm.

The Examples illustrate the invention in more detail.

EXAMPLE 1

Preparation of N-(n-butyl)-O-propyl-3-[7-isopropyl-1-methylazulen-4-yl]urethane (Compound No. 2)

150 g of (0.15 mol) of n-butyl isocyanate were added dropwise at room temperature to a solution of 9.6 g (0.04 mol) of 7-isopropyl-1-methyl-4-(3-hydroxypropyl) azulene in 100 ml of methylene chloride, and the reaction solution was then refluxed for 5 hours. The solvent was then distilled off, and the residue was chromatographed over silica gel (methylene chloride/acetone). 7.0 g (51%) of the urethane was obtained as a blue, highly viscous oil (Compound No. 2).

Physical data: IR (KBr): $\bar{\nu}=3336$ (broad, NH), 2958, 2931, 2871, 1699 s (C=O), 1527, 1465, 1387, 1251, 1142, 1061, 1030, 784 cm$^{-1}$; $^1$H-NMR (CDCl$_3$): $\delta=0.90$ t(3H), 1.25–1.55 m, 1.38 d(6H), 2.17 q(2H), 2.66 s(3H), 3.08 q(1H), 3.17 m, 4.5 t(2H), 4.46 broad (NH), 6.98 d(1H), 7.28 d(1H), 7.39 d(1H), 7.61 d(1H), 8.18 s(1H); $^{13}$C-NMR (CDCl$_3$): $\delta=12.86$, 13.69, 20.00, 24.75 (2C), 30.79, 32.34, 34.65, 38.34, 41.04, 64.71, 112.40, 124.51, 125.44, 133.26, 135.15, 136.48, 136.59, 137.41, 140.02, 147.92, 156.82; MS:m/e=341 (100%, M$^\oplus$), 326, 312, 298, 258, 240, 224 (45%), 209, 198 (60%), 181.

The method of Example 1 was also used to prepare the azulene derivatives listed in Table 1. Their structure is confirmed by IR, $^1$H-NMR, $^{13}$C-NMR and MS spectra.

TABLE 1

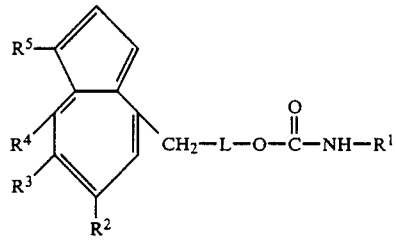

| Compound No. | L—O—C(O)NH—R$^1$ | R$^2$ | R$^3$ | R$^4$ | R$^5$ | MS [M$^\oplus$/100%] | IR ($\bar{\nu}$/cm$^{-1}$) [NH, C=O] |
|---|---|---|---|---|---|---|---|
| 1 | (CH$_2$)$_2$OC(O)NH—C$_6$H$_5$ | H | CH(CH$_3$)$_2$ | H | CH$_3$ | 361 | 3340, 1699 |
| 2 | (CH$_2$)$_2$OC(O)NH-nC$_4$H$_9$ | H | CH(CH$_3$)$_2$ | H | CH$_3$ | 341 | 3340, 1695 |
| 3 | (CH$_2$)$_2$OC(O)NH-tC$_4$H$_9$ | H | CH(CH$_3$)$_2$ | H | CH$_3$ | 341 | 3340, 1696 |
| 4 | (CH$_2$)$_2$OC(O)NH-iC$_4$H$_9$ | H | CH(CH$_3$)$_2$ | H | CH$_3$ | 327 | 3340, 1695 |
| 5 | (CH$_2$)$_2$OC(O)NH—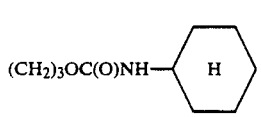 | H | CH(CH$_3$)$_2$ | H | CH$_3$ | 367 | 3340, 1697 |
| 6 | (CH$_2$)$_2$OC(O)NH-nC$_{18}$H$_{37}$ | H | CH(CH$_3$)$_2$ | H | CH$_3$ | 537 | 3340, 1693 m.p. 37–38° C. |
| 7 | (CH$_2$)$_3$OC(O)NH—C$_6$H$_5$ | H | CH(CH$_3$)$_2$ | H | CH$_3$ | 375 | 3340, 1696 |
| 8 | (CH$_2$)$_3$OC(O)NH-nC$_4$H$_9$ | H | CH(CH$_3$)$_2$ | H | CH$_3$ | 355 | 3340, 1697 |
| 9 | (CH$_2$)$_3$OC(O)NH-tC$_4$H$_9$ | H | CH(CH$_3$)$_2$ | H | CH$_3$ | 355 | 3340, 1695 |
| 10 | (CH$_2$)$_3$OC(O)NH-iC$_3$H$_7$ | H | CH(CH$_3$)$_2$ | H | CH$_3$ | 341 | 3340, 1695 |
| 11 | (CH$_2$)$_3$OC(O)NH—phenyl | H | CH(CH$_3$)$_2$ | H | CH$_3$ | 381 | 3340, 1696 |
| 12 | (CH$_2$)$_3$OC(O)NH-nC$_{18}$H$_{37}$ | H | CH(CH$_3$)$_2$ | H | CH$_3$ | 551 | 3340, 1694 |
| 13 | CHCH$_2$OC(O)NH—C$_6$H$_5$<br>\|<br>CH$_3$ | H | CH(CH$_3$)$_2$ | H | CH$_3$ | 375 | 3340, 1698 |

TABLE 1-continued

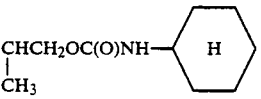

| Compound No. | L—O—C(O)NH—R¹ | R² | R³ | R⁴ | R⁵ | MS [M⊕/100%] | IR ($\nu$/cm$^{-1}$) [NH, C=O] |
|---|---|---|---|---|---|---|---|
| 14 | CHCH₂OC(O)NH-nC₄H₉<br>\|<br>CH₃ | H | CH(CH₃)₂ | H | CH₃ | 355 | 3340, 1698 |
| 15 | CHCH₂OC(O)NH-tC₄H₉<br>\|<br>CH₃ | H | CH(CH₃)₂ | H | CH₃ | 355 | 3340, 1696 |
| 16 | CHCH₂OC(O)NH-iC₃H₇<br>\|<br>CH₃ | H | CH(CH₃)₂ | H | CH₃ | 341 | 3340, 1697 |
| 17 | CHCH₂OC(O)NH—⟨C₆H₁₁⟩<br>\|<br>CH₃ | H | CH(CH₃)₂ | H | CH₃ | 381 | 3340, 1696 |
| 18 | CHCH₂OC(O)NH-nC₁₈H₃₇<br>\|<br>CH₃ | H | CH(CH₃)₂ | H | CH₃ | 551 | 3340, 1695 |
| 19 | CHCH₂OC(O)NH-nC₄H₉<br>\|<br>C₂H₅ | H | CH(CH₃)₂ | H | CH₃ | 369 (70%)<br>198 (100%) | 3340, 1698 |
| 20 | CHCH₂OC(O)NH-tC₄H₉<br>\|<br>C₂H₅ | H | CH(CH₃)₂ | H | CH₃ | 369 | 3340, 1696 |
| 21 | CHCH₂OC(O)NH-iC—H₇<br>\|<br>C₂H₅ | H | CH(CH₃)₂ | H | CH₃ | 355 | 3340, 1697 |
| 22 | CH—CH₂OC(O)NH—⟨C₆H₁₁⟩<br>\|<br>C₂H₅ | H | CH(CH₃)₂ | H | CH₃ | 395 | 3340, 1696 |
| 23 | CH—CH₂OC(O)NH-nC₁₈H₃₇<br>\|<br>C₂H₅ | H | CH(CH₃)₂ | H | CH₃ | 565 | 3340, 1695 |
| 24 | CH—CH₂OC(O)NH-nC₄H₉<br>\|<br>C₂H₅ | H | CH(CH₃)₂ | H | CH₃ | 417 (40%)<br>198 (100%) | 3340, 1696 |
| 25 | (CH₂)₂OC(O)NH-nC₄H₉ | CH₃ | H | CH₃ | H | | 3350, 1690 |

EXAMPLE 2

Preparation of the bis(O-propyl-3-[7-isopropyl-1-methylazulene-4-yl]-N-(n-butyl)urethane)squaric acid dye (Compound No. 27)

6.8 g (0.002 mol) of N-(n-butyl)-O-propyl-3-[7-isopropyl-1-methylazulene-4-yl]urethane (Example 1) and 2.3 g (0.02 mol) of squaric acid were refluxed in 160 ml of 1:1 toluene/n-butanol for 5 hours. The solvent was drawn off under reduced pressure, leaving a green oil which was chromatographed over silica gel (methylene chloride/acetone). Yield: 2.3 g (30%) of metallically bright crystals.

Physical data:

Melting point: 155°–156° C.

UV (CH₂Cl₂): $\lambda$max=770 nm ($\epsilon$=112 250); IR (KBr): $\bar{\nu}$=3325 (NH), 2958, 2928, 2862, 1691, 1609, 1592, 1543, 1432, 1387, 1326s, 1248, 1217, 1024, 916, 765, 587 cm$^{-1}$;

¹H-NMR (CDCl₃): $\delta$=0.84 t (6H), 1.13–1.45 m(8H), 1.48 d(12H), 1.91 q(4H), 2.55 s(6H), 2.98 q(4H), 3.11 q(2H), 3.88 m(4H), 3.98 m(4H), 4.74 broad (2NH), 7.45 d(2H), 7.58 d(2H), 8.09 s(2H), 8.82 s(2H);

13C-NMR (CDCl3): δ=12.96 (2C), 13.66 (2C), 19.95 (2C), 24.24 (4C), 31.02 (2C), 32.16 (2C), 36.30 (2C), 38.40 (2C), 40.91 (2C), 63.97 (2C), 121.66 (2C), 130.82 (2C), 133.98 (2C), 134.55 (2C), 138.24 (2C), 139.85 (2C), 141.83 (2C), 147.50 (2C), 150.27 (2C), 156.01 (2C), 156.72 (2C), 179.53, 182.75, 183.24 (2C);

MS: m/e = 762, 760 (40%)

The method of Example 2 was also used to prepare the squaric acid dyes listed in Table 2, which were additionally characterized by $^1$H-NMR, $^{13}$C-NMR, IR and MS spectra.

TABLE 2

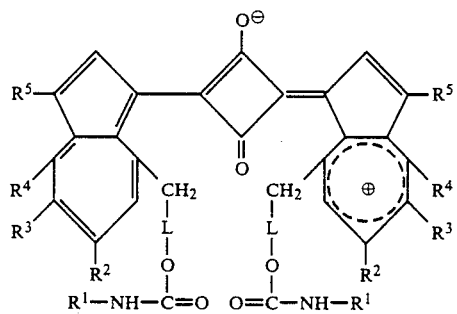

| Compound No. | L—O—C(O)NH—R$^1$ | R$^2$ | R$^3$ | R$^4$ | R$^5$ | λ max [nm] (in CH$_2$Cl$_2$) | Melting point [°C.] |
|---|---|---|---|---|---|---|---|
| 26 | (CH$_2$)$_2$OC(O)NH—C$_6$H$_5$ | H | CH(CH$_3$)$_2$ | H | CH$_3$ | 770 | 257-258 |
| 27 | (CH$_2$)$_2$OC(O)NH-nC$_4$H$_9$ | H | CH(CH$_3$)$_2$ | H | CH$_3$ | 770 | 155-156 cf. Example 2 |
| 28 | (CH$_2$)$_2$OC(O)NH-tC$_4$H$_9$ | H | CH(CH$_3$)$_2$ | H | CH$_3$ | 768 | 190-192 |
| 29 | (CH$_2$)$_2$OC(O)NH-iC$_3$H$_7$ | H | CH(CH$_3$)$_2$ | H | CH$_3$ | 768 | 143-144 |
| 30 | (CH$_2$)$_2$OC(O)NH—cyclohexyl | H | CH(CH$_3$)$_2$ | H | CH$_3$ | 768 | 197 |
| 31 | (CH$_2$)$_2$OC(O)NH-nC$_{18}$H$_{37}$ | H | CH(CH$_3$)$_2$ | H | CH$_3$ | 770 | 100-101 |
| 32 | (CH$_2$)$_3$OC(O)NH—C$_6$H$_5$ | H | CH(CH$_3$)$_2$ | H | CH$_3$ | 769 | 238-242 |
| 33 | (CH$_2$)$_3$OC(O)NH-nC$_4$H$_9$ | H | CH(CH$_3$)$_2$ | H | CH$_3$ | 768 | 133-134 |
| 34 | (CH$_2$)$_3$OC(O)NH-tC$_4$H$_9$ | H | CH(CH$_3$)$_2$ | H | CH$_3$ | 768 | 157-158 |
| 35 | (CH$_2$)$_3$OC(O)NH-iC$_3$H$_7$ | H | CH(CH$_3$)$_2$ | H | CH$_3$ | 768 | 154-155 |
| 36 | (CH$_2$)$_3$OC(O)NH—cyclohexyl | H | CH(CH$_3$)$_2$ | H | CH$_3$ | 768 | 185-186 |
| 37 | (CH$_2$)$_3$OC(O)NH-nC$_{18}$H$_{37}$ | H | CH(CH$_3$)$_2$ | H | CH$_3$ | 769 | 94-98 |
| 38 | CHCH$_2$OC(O)NH—C$_6$H$_5$ <br> \| <br> CH$_3$ | H | CH(CH$_3$)$_2$ | H | CH$_3$ | 772 | 208-212 |
| 39 | CHCH$_2$OC(O)NH-nC$_4$H$_9$ <br> \| <br> CH$_3$ | H | CH(CH$_3$)$_2$ | H | CH$_3$ | 773 | 185-187* |
| 40 | CHCH$_2$OC(O)NH-tC$_4$H$_9$ <br> \| <br> CH$_3$ | H | CH(CH$_3$)$_2$ | H | CH$_3$ | 773 | 174-175* |
| 41 | CHCH$_2$OC(O)NH-iC$_3$H$_7$ <br> \| <br> CH$_3$ | H | CH(CH$_3$)$_2$ | H | CH$_3$ | 773 | 168-169* |
| 42 | CHCH$_2$OC(O)NH—cyclohexyl <br> \| <br> CH$_3$ | H | CH(CH$_3$)$_2$ | H | CH$_3$ | 773 | 197-198* |
| 43 | CHCH$_2$OC(O)NH-nC$_{18}$H$_{37}$ <br> \| <br> CH$_3$ | H | CH(CH$_3$)$_2$ | H | CH$_3$ | 773 | 93-74* |
| 44 | CHCH$_2$OC(O)NH-nC$_4$H$_9$ <br> \| <br> C$_2$H$_5$ | H | CH(CH$_3$)$_2$ | H | CH$_3$ | 772 | 209* |

TABLE 2-continued

| Compound No. | L—O—C(O)NH—R$^1$ | R$^2$ | R$^3$ | R$^4$ | R$^5$ | λ max [nm] (in CH$_2$Cl$_2$) | Melting point [°C.] |
|---|---|---|---|---|---|---|---|
| 45 | CHCH$_2$OC(O)NH-tC$_4$H$_9$<br>\|<br>C$_2$H$_5$ | H | CH(CH$_3$)$_2$ | H | CH$_3$ | 772 | 201–202* |
| 46 | CHCH$_2$OC(O)NH-iC$_3$H$_7$<br>\|<br>C$_2$H$_5$ | H | CH(CH$_3$)$_2$ | H | CH$_3$ | 770 | 90–115* |
| 47 | CHCH$_2$OC(O)NH—⟨C$_6$H$_{11}$⟩<br>\|<br>C$_2$H$_5$ | H | CH(CH$_3$)$_2$ | H | CH$_3$ | 770 | 60–85* |
| 48 | CHCH$_2$OC(O)NH-C$_{18}$H$_{37}$<br>\|<br>C$_2$H$_5$ | H | CH(CH$_3$)$_2$ | H | CH$_3$ | 774 | [oil]* |
| 49 | CHCH$_2$OC(O)NH-nC$_4$H$_9$<br>\|<br>C$_6$H$_5$ | H | CH(CH$_3$)$_2$ | H | CH$_3$ | 774 | 102* |
| 50 | (CH$_2$)$_2$OC(O)NH—C$_4$H$_9$ | CH$_3$ | H | CH$_3$ | H | 720 | |

*The product is a mixture of isomers or is not analytically pure.

EXAMPLE 3

A 5% strength by weight solution of dye 27 in toluene was syringed onto a polymethyl methacrylate disk rotating at about 2000 rpm, and the remaining solvent was then spun off at 5000 rpm. The result obtained was a homogeneous, highly reflective dye layer which was very readily writable with a semiconductor laser (λ=830 nm). The data can be read back with good contrast.

EXAMPLE 4

A 3% strength by weight solution of dye 27 containing 30% by weight, based on the level of dissolved solids in the solution, of polymethyl methacrylate was spincoated by the method of Example 3 onto a grooved polycarbonate disk. The result obtained was a homogeneous, highly reflective dye layer which firmly adhered to the substrate, which gave a good picture of the tracking grooves on the substrate, and which was very readily writable with a semiconductor laser (λ=830 nm). The written information was stable under high temperature and humidity conditions and was readable back as often as desired with good contrast.

EXAMPLE 5

A 2% by weight solution of dye 27 in 1:1 propanol/diacetone alcohol containing, based on the level of dissolved solids in the solution, 10% by weight of a phenolic resin as binder and 5% by weight of 4-octyl-4'-fluorodiphenyldithiolenenickel as a stabilizer was spincoated as in Example 3 onto a grooved polycarbonate disk. The storage layer obtained was comparable to that of Example 3 in all respects but was more stable to UV light.

EXAMPLE 6

A 2% strength by weight solution of dye 48 in toluene containing, based on the level of dissolved solids in the solution, 10% by weight of polymethyl methacrylate and 5% by weight of biscampheratodithiolenenickel was spincoated by the method of Example 3 onto a glass disk. The dye layer obtained was homogeneous and showed high background reflectivity. It was readily writable with a semiconductor laser (λ=780 nm). The written data are stable under the customary test conditions and can be read back as often as desired.

We claim:

1. An azulenesquaric acid dye having the formula:

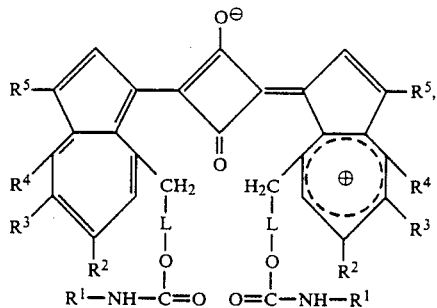

(I)

where

L is $C_1$-$C_{12}$-alkylene or $C_1$-$C_{12}$-alkylene substituted by phenyl, $R^1$ is $C_1$-$C_{20}$-alkyl, $C_5$-$C_7$-cycloalkyl, phenyl or phenyl substituted by $C_1$-$C_4$-alkyl, $C_1$-$C_4$-alkoxy or halogen, $R^2$, $R^3$, $R^4$ and $R^5$ are identical or different and are each independently of the others hydrogen or $C_1$-$C_{12}$-alkyl, $C_1$-$C_{12}$ alkyl, substituted by halogen, $C_1$-$C_4$-alkoxy, phenyl, phenyl substituted by $C_1$-$C_4$-alkyl, $C_1$-$C_4$-alkoxy or halogen, $C_1$-$C_{12}$-alkoxycarbonyl or cyano, with the proviso that when $R^5$ is hydrogen the positions of the substituents $CH_2$—L—O—CO—$NHR^1$ and $R^4$ on an azulene ring also are within a ring in either or both of the azulene rings.

2. An azulenesquaric acid dye as claimed in claim 1, wherein $R^2$, $R^3$, $R^4$ and $R^5$ are each $C_1$-$C_6$-alkyl.

3. An azulenesquaric acid dye as claimed in claim 1, wherein $R^2$ and $R^4$ are each methyl and $R^3$ and $R^5$ are each hydrogen.

4. An azulenesquaric acid dye as claimed in claim 1, wherein $R^2$ and $R^4$ are each hydrogen, $R^3$ is isopropyl and $R^5$ is methyl.

* * * * *

UNITED STATES PATENT AND TRADEMARK OFFICE
CERTIFICATE OF CORRECTION

PATENT NO. : 4,990,649

DATED : February 5, 1991

INVENTOR(S) : Wolfgang Schrott et al

It is certified that error appears in the above-identified patent and that said Letters Patent is hereby corrected as shown below:

Title page item (75):

The last inventor's name is spelled incorrectly, should be

--Harald Kuppelmaier--.

Signed and Sealed this

Tenth Day of November, 1992

Attest:

DOUGLAS B. COMER

*Attesting Officer*     *Acting Commissioner of Patents and Trademarks*